US012655094B2

(12) United States Patent
Moustafa

(10) Patent No.: US 12,655,094 B2
(45) Date of Patent: Jun. 16, 2026

(54) CANNABINOID SULFATE ESTERS, THEIR SALTS AND USES THEREOF

(71) Applicant: LONDON PHARMACEUTICALS AND RESEARCH CORPORATION, London (CA)

(72) Inventor: Mahmoud Mohamed Abdrabo Moustafa, London (CA)

(73) Assignee: London Pharmaceuticals and Research Corporation, London (CA)

( * ) Notice: Subject to any disclaimer, the term of this patent is extended or adjusted under 35 U.S.C. 154(b) by 847 days.

(21) Appl. No.: 17/796,901

(22) PCT Filed: Feb. 5, 2021

(86) PCT No.: PCT/CA2021/050132

§ 371 (c)(1),
(2) Date: Aug. 2, 2022

(87) PCT Pub. No.: WO2021/155474

PCT Pub. Date: Aug. 12, 2021

(65) Prior Publication Data

US 2023/0339850 A1 Oct. 26, 2023

Related U.S. Application Data

(60) Provisional application No. 62/970,764, filed on Feb. 6, 2020.

(51) Int. Cl.

| | |
|---|---|
| ***C07C 305/24*** | (2006.01) |
| ***A23L 2/52*** | (2006.01) |
| ***A23L 33/105*** | (2016.01) |
| ***A61K 31/00*** | (2006.01) |
| ***C07D 311/80*** | (2006.01) |

(52) U.S. Cl.

CPC .............. *C07C 305/24* (2013.01); *A23L 2/52* (2013.01); *A23L 33/105* (2016.08); *A61K 31/658* (2023.05); *C07D 311/80* (2013.01)

(58) Field of Classification Search

CPC .... C07C 305/24; C07D 311/80; A23L 33/105
See application file for complete search history.

(56) References Cited

U.S. PATENT DOCUMENTS 5,210,081 A 5/1993 Raveendranath et al.

FOREIGN PATENT DOCUMENTS

| | | | |
|---|---|---|---|
| WO | WO2004/043946 | A1 | 5/2004 |
| WO | WO2017216362 | A1 | 12/2017 |
| WO | WO2018/096504 | A1 | 5/2018 |

OTHER PUBLICATIONS

Takada, Atsushi: Researches on Chemotherapeutic Drugs against Viruses: pharmaceutical institute, Keio-Gijuku University, UDC 615.778 [547.263'53'233], p. 908.

Smith, N.H.P.: Faculty of Technology, University of Machester, 4-t-Butylthioacetophenone: its Ultraviolet Absorption Spectrum, and Cyanohydrin Dissociation Constant, [1965], Notes, 4599, Published Jan. 1, 1965.

Dawson, Daniel A., et al: Department of Chemistry, University of Toronto, Received Jul. 15, 1974; Investigations of Substituent Effects by nuclear Magnetic Resonance Spectroscopy and All-valence Electron Molecular Orbital Calculations. IV. 4-substitued Phenylacetylenes.

Tarbell, D.S., et al, 1456, vol. 68—Synthesis in the Thionaphthene Series, Contribution from the Department of Chemistry of the University or Rochester: Streptomyces Antibiotics. VIII. Isolation of Streptomycin: Frederick A. Kuehl, Peck, Hoffhine, Graber and Folkers.

Abbady, Sh.H. Abdel-Hafez, et al: Syntheses of New Unsymmetrical and Symmetrical Diarylsulphides and Diarylsulphones Containing Thiazolinyl and Thiazolidinonyl Moieties Using 4,4'-Diacetyldiphenylsulphide, Molecules 2003, 8, 622-641, ISSN 1420-3049.

Vijesh, Islor, et al; Hantzsch reaction: Synthesis and characterization of some new 1,4-dihydropyridine derivatives as potent antimicrobial and antioxidant agents: European Journal of Medicinal Chemistry, Elsevier, 46(2011) 5591-5597.

Sharghi , et al: Faculty of Pharmacy, University of Tehran; Fluorothiophenols and Their Derivatives; Journal of Chemical and Engineering Data, vol. 8, No. 2, Apr. 1963 p. 276-278.

CAS Registry No. 1562620-64-7, 2-[1-[4-(Methylthio)phenyl] ethylidene]hydrazin ecarboximidamide, Mar. 3, 2021; Zhejiang Aoda Yiyao Youxian Gongsi (Distributor Name).

CAS Registry 1562886-88-7, 2-: [1-[4-(Methylthio)phenyl]ethylid ene]hydrazinecarbothioamide; Mar. 3, 2021, Zhejiang Aoda Yiyao Youxian Gongsi (Distributor Name).

CAS Registry 1562849-10-8 2-[1-[4-(Methylsulfonyl) phenyl]ethylidene]hydrazinecarbothioamide; Mar. 3, 2021—Zhejiang Aoda Yiyao Youxian Gongsi (Distributor Name).

Cousson, Alain: Structure of 5-11-(Diaminomethylenehydrazono)ethyll-4-methyl-2-methylthiopyrimidine: Acta Cryst. (1993). C49, 1670-1673: Laboratoire Ldon Brillouin (CEA-CNRS), CE Saclay, 91191 Gif-sur-Yvette Cedex, France.

Nishimura, Yoshii, Toku and Mochizuki: Amidinohydrazone . . . Alkoxybenzalacetone: Antibacterial Activities of Amidinohydrazones I. Antibacterial Actrivities of Alkoxybenzalacetone Amidinohydrazones: UDC, 547.574.3.09: 615.28.015.11: School of hygienic Sciences, Kitasato University, Dec. 2, 1972.

(Continued)

*Primary Examiner* — Sikarl A Witherspoon

(57) ABSTRACT

Cannabinoid sulfate esters, their soluble salts and stable formulations thereof, as well as their edible, beverage and medicinal applications. The cannabinoid sulfate ester salts may be used as drugs or prodrugs for treating various conditions related to the modulation or biased modulation of cannabinoid receptors, including but not limited to, pain and inflammation, cancer, glaucoma, neurodegenerative disorders, multiple sclerosis, renal fibrosis, fibrotic disorder, addiction, motor function disorders and gastrointestinal and metabolic disorders.

40 Claims, No Drawings

(56) References Cited

OTHER PUBLICATIONS

Elsohly, Gul and Walker: Pharmacokinetics and Tolerability of Δ9-THC-Hemisuccinate in a Suppository Formulation as an Alternative to Capsules for the Systemic Delivery of Δ9-THCMed Cannabis Cannabinoids, Preclinic Science and Clinical Studies—Research Article: 2018: 1:44-53, Published: Jun. 12, 2018.
Juntunen, et al: A nandamide prodrugs 1. Water-soluble phosphate esters of arachidonylethanolamide and R-methanandamide, Science Direct, Elsevier, Department of Pharmaceutical Chemistry, University of Kuopio, Finland . . . European Journal of Pharmaceutical Sciences 19 (2003) 37-43.
Watanabe, K. et al: Chem.Pharm. Bull. 27/12, 1979, 3009-3014.

CANNABINOID SULFATE ESTERS, THEIR SALTS AND USES THEREOF

FIELD OF THE INVENTION

The present invention relates to the field of medicinal chemistry and, in particular, to cannabinoid sulfate esters, their salts and uses for treating, alleviating or reducing symptoms of illnesses in human or animal subjects.

BACKGROUND

The endocannabinoid system mediates many important physiological functions including neuroplasticity and learning, emotion and motivation, appetite, and GI motility as well as immunomodulation. There are at least two types of G-protein coupled cannabinoid receptors that have been isolated and fully characterized in mammals: a) CB1: located centrally and peripherally and involved mainly in neurotransmitters homeostasis; and b) CB2: located peripherally and linked with the immune system. These receptors represent a promising therapeutic targets for various conditions including chronic pain, inflammation, neurodegenerative disorders, epilepsy, addiction, insomnia, cancer, obesity, and anorexia. Designing specific cannabinoid ligands to manage these conditions has received increased interest in recent years.

The cannabinoid receptors can be modulated by a heteromorphic group of compounds, so-called cannabinoids. They can be classified into three main groups: a) endogenous or endocannabinoids (e.g. arachidonoylethanolamide); b) natural or phytocannabinoids, which are the active constituents of *Cannabis* species (e.g. delta-9-tetrahydrocannabinol (THC) and cannabidiol (CBD)); and c) synthetic (e.g. nabilone), which are illustrated in Table 1, below.

TABLE 1

Representative examples of cannabinoids

| Cannabinoids class | Examples |
|---|---|
| A. Endogenous | 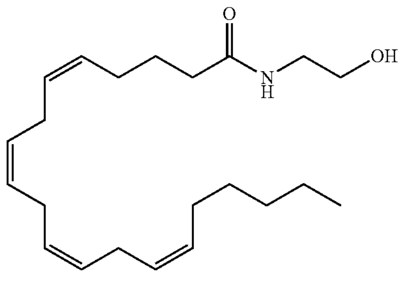 Arachidonoylethanolamide |
| B. Natural | 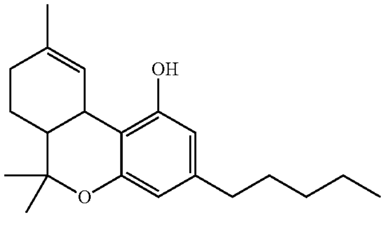 THC |
| | 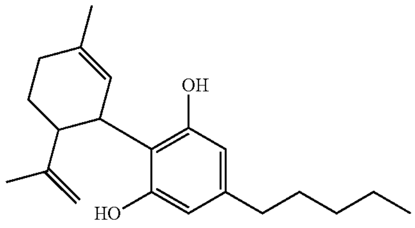 CBD |
| C. Synthetic | 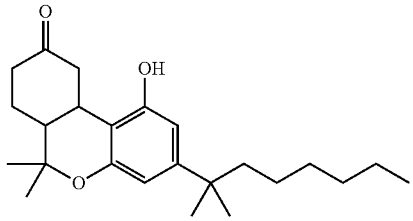 Nabilone |

The clinical utility of cannabinoids has been documented in the treatment of many conditions. Sativex®, by GW Pharmaceuticals, is a buccal spray of THC and CBD in a 1:1 mixture and has been approved in many countries as an adjunctive treatment of neuropathic pain and spasticity associated with multiple sclerosis in adults. Cesamet™ (nabilone), by Bausch Health Co., is a synthetic cannabinoid for oral administration as an antiemetic through a CB1 receptor mediated interaction.

Despite their clinical potential, natural cannabinoids (phytocannabinoids) extracted from *C. sativa* are highly lipophilic (possessing log P values of 6-7), sparingly soluble in water (aqueous solubility=2-10 μg/mL at 23° C.), chemically unstable (particularly in solution via light, temperature, and auto-oxidation), and gummy in nature with erratic absorption, a delayed onset, extensive first-pass metabolism, high plasma protein binding, large volume of distribution and low systemic bioavailability after oral administration, leading to unpredictable time course of action and long half-life ($t_{1/2}$). In addition, the clinical benefits of smoked herb are short and associated with mucosal damage, serious adverse effects, and exposure to carcinogenic by-products. Furthermore, THC can cross the blood brain barrier (BBB) and activate central CB1 producing unwanted psychotropic effects. In an attempt to overcome these limitations, a variety of formulations and drug delivery approaches have been developed including co-solvency, complexation, surfactant and carrier-assisted methods, thus far, with limited success.

On the other hand, several synthetic derivatives and pro-drugs have been reported and widely used to modulate CB1 and CB2. For example, WO 2017/216362 A1 of Full Spectrum Laboratories Ltd. discloses cannabinoid prodrugs, and their production, formulations and uses. This reference discloses only esters of organic and amino acids, for example, succinic acid and valine.

WO 2004/043946 A1 of Mallinckrodt Inc. discloses highly crystalline aryl sulfonic THC esters. They can be recrystallized for purification and are stable at room temperature in air, allowing for indefinite storage and recovery of pure THC upon hydrolysis. This reference does not disclose any pharmacological actions or clinical utilities for these esters.

Watanabe et al (Chem Pharm Bull 27: 3009-3014, 1979) reported the chemical synthesis of delta-8-THC glucuronide and sulfate esters to study their hydrolysis, acute toxicity and metabolic disposition in rats. However, no pharmacological or biological utility is described for any of theses esters.

Juntunen et al (Eur. J. Pharm. Sci. 19, 37-43, 2003) reported the synthesis of a water-soluble phosphate ester pro-drug of anandamide. The phosphate functional group increased the aqueous solubility of the parent endocannabinoids by >16 500-fold at pH 7.4 and reduced the intraocular pressure in normotensive rabbit. The study did not investigate any of the more clinically useful phytocannabinoids and did not report any other pharmacological actions or clinical uses of this phosphate ester of anandamide or its salts.

To minimize the limitations in the prior art, there exists a demand for new cannabinoid derivatives with optimized physicochemical, pharmacokinetic (PK) and pharmacodynamic (PD) properties for specific clinical applications.

SUMMARY OF THE INVENTION

The cannabinoid compounds, according to the present invention, are labile sulfate esters of cannabinoids and their salts. The esters are sensitive to enzymatic or chemical hydrolysis within the animal or human body, so as to release the parent cannabinoids and thereby modulate the endocannabinoid system.

In one embodiment, the cannabinoid compounds are sulfate or hemisulfate esters of a cannabinoid and their salts with inorganic or organic bases.

In another embodiment, the inorganic or organic bases are selected from the group consisting of: NaOH, KOH, LiOH, $Ca(OH)_2$, $Mg(OH)_2$, erbumine, a cyclic amine, acyclic amine, ethanol amine derivative, aromatic amine, aliphatic amine, amino sugar, and amino acid.

In another embodiment, the cannabinoid compounds are sulfate or hemisulfate esters of THC, represented by the general formula I:

Formula I

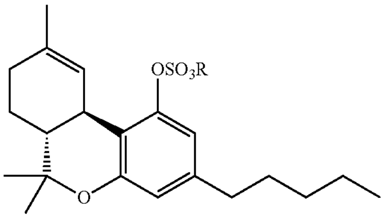

wherein R is selected from the group consisting of: H, a second cannabinoid, a synergistic compound, a non-synergistic active compound, and an inactive side group.

In another embodiment, the cannabinoid compounds are sulfate or hemisulfate esters of CBD, represented by the general formula II and III:

Formula II

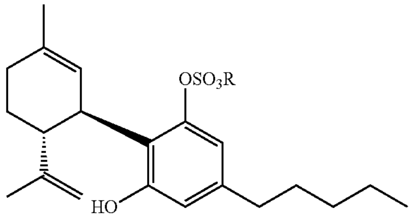

Formula III

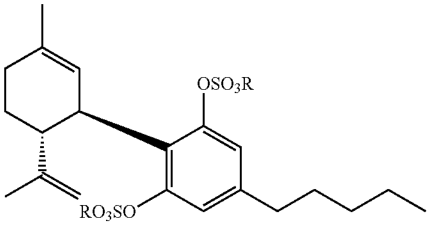

wherein R is selected from the group consisting of: H, a second cannabinoid, a second active compound, and an inactive side group.

In another embodiment, the second cannabinoid has a hydroxyl, amino, or phenolic functional group. The second cannabinoid may be selected from the group consisting of THC, CBD, cannabinodiol (CBND), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), and cannabitriol (CBT), and their derivatives and analogues or related chemical structures.

In another embodiment, the second active compound has a hydroxyl, amino, or phenolic functional group. The second active compound may be selected from the group consisting of acetaminophen, ibuprofen, morphine, caffeic acid, L-DOPA, coumaric acid, quercetin, flavonoids, salicylic acid, thymol, eugenol, entacapone, tolcapone, estrogens, androgens and corticosteroids.

In another embodiment, the cannabinoid compounds are sulfate ester salts of THC, represented by the general formula IV:

Formula IV

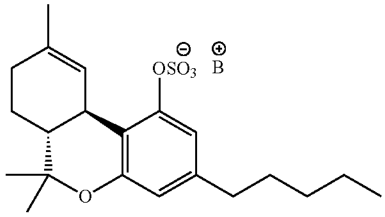

wherein B is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

In another embodiment, the cannabinoid compounds are sulfate ester salts of CBD, represented by the general formula V and VI:

Formula V

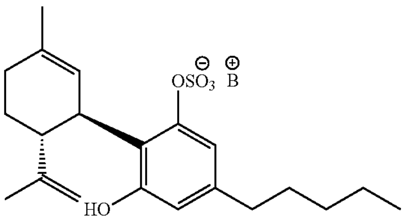

Formula VI

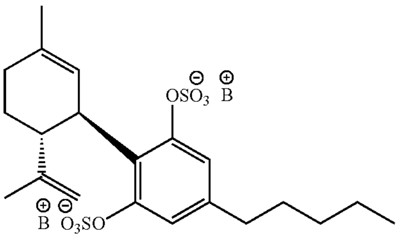

wherein B is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

Certain embodiments of the cannabinoid compounds, according to the present invention, may demonstrate one or more desirable features, including improved stability, higher solubility, chemical stability and optimum PK and/or PD properties.

Water-soluble cannabinoid sulfate esters, according to the present invention, may be used for edible, beverage, and medicinal applications. The esters may be hemi esters, full esters or salts.

In another embodiment, the cannabinoid sulfate esters are in the form of water-soluble salts. The salts may be of alkali metals or organic bases.

Another embodiment of the present invention is a method of producing a cannabinoid compound by synthetic or semisynthetic methods. The method includes the following steps:

a. Dissolving a cannabinoid having at least one hydroxyl group in a suitable aprotic organic solvent.

b. Reacting the cannabinoid solution with a sulfate transfer reagent in the presence of an alkali or an organic base.

c. Heating the reaction under conventional heating, microwave heating, or sonication to produce a product.

d. Purify the product using flash chromatography, extraction, distillation, sublimation or crystallization.

In another embodiment, the aprotic organic solvent is selected from the group consisting of pyridine, toluene, tetrahydrofuran, halogenated hydrocarbons, xylenes, and hexanes.

In another embodiment, the sulfate transfer reagent is selected from the group consisting of protected and free chlorosulfonic acid, protected and free sulfonic acid, protected and free sulfuric acid, sulfur trioxide, sulfur trioxide complexes, sulfur trioxide pyridine, alkali metal disulfate, sulfonyl imidazolium salts, N-hydroxysuccinimide-sulfate and tributylsulfoammonium betaine.

In another embodiment, pyridine salt of CBD sulfate ester may be produced according to the method illustrated in Formula VII, below, to obtain the target sulfate in quantitative yield (90-99%) and analytical purity (95-98%). The temperature is between 65-90° C., the pressure is between 5-20 bar, and the reaction time is between 2-4 hrs in pyridine.

Formula VII

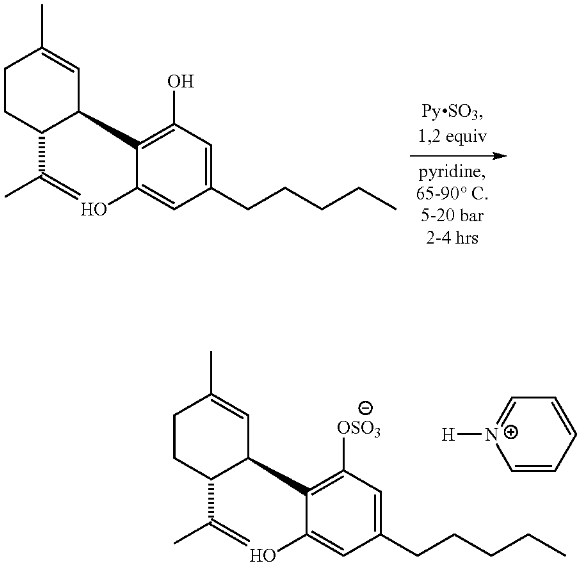

In another embodiment, various salts and forms of CBD sulfate esters may be produced according to the method illustrated in Formula VIII, below. The pyridine counter ion may be replaced by other selected bases in quantitative yield (95-99%) and analytical purity (95-98%) as amorphous powder when stirred with 1.2 equiv of the selected base in aqueous solutions and as a crystalline compound in non aqueous solutions.

Formula VIII

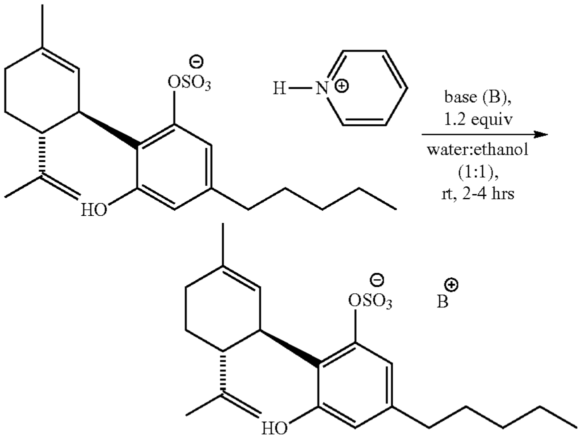

In another embodiment, a morpholine salt of THC sulfate ester may be produced according to the method illustrated in Formula IX, below.

Formula IX

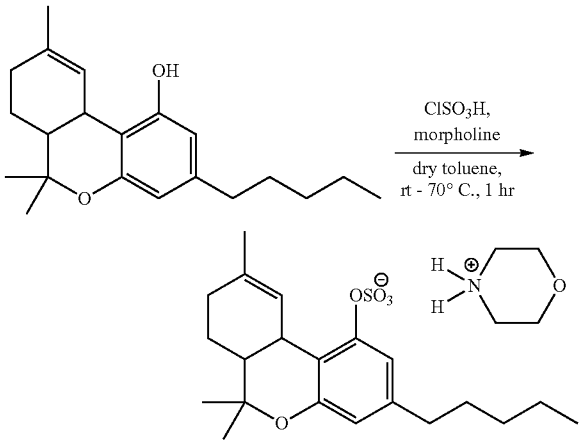

In another embodiment, a piperazine salt of THC sulfate ester may be produced according to the method illustrated in Formula X, below.

Formula X

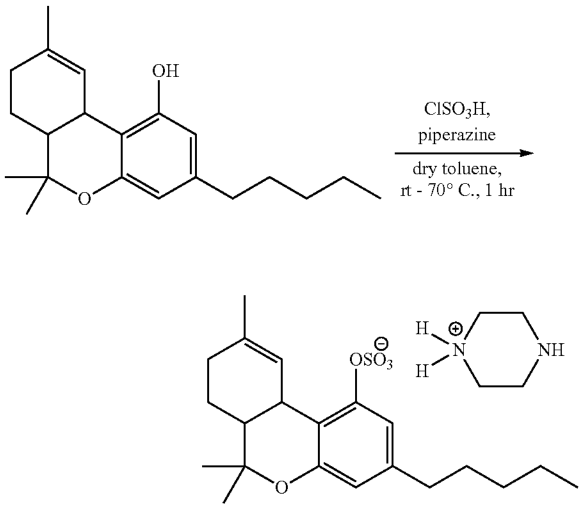

Another embodiment relates to a method to produce cannabinoid sulfate esters, by enzymatic methods including microbial, synthetic biology and genetic manipulation of *Cannabis* sp, according to the method illustrated in Formula XI, below.

Formula XI

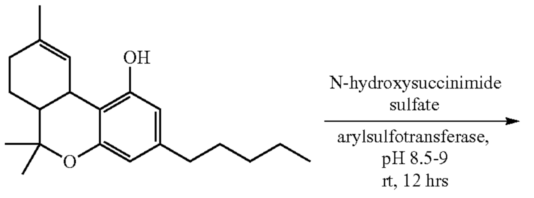

-continued

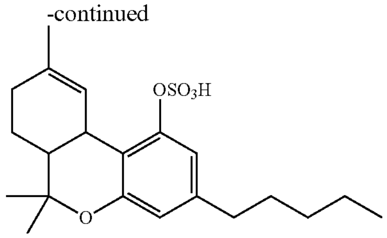

In certain embodiments, the cannabinoid sulfate esters may act on either or both peripheral and central tissues.

In another embodiment, the cannabinoid sulfate esters are peripherally restricted, such that they lack the central psychoactive properties of THC.

In another embodiment, the cannabinoid sulfate esters may be used to manage several conditions including pain and inflammation, cancer, glaucoma, neurodegenerative disorders, multiple sclerosis, renal fibrosis, fibrotic disorder, addiction, motor function disorders and gastrointestinal and metabolic disorders and other conditions that respond to cannabinoid receptor modulation or are otherwise known to be treatable by administration of one or more cannabinoids.

In another embodiment, the cannabinoid sulfate esters may be used for both human and animal applications.

In certain embodiments, the cannabinoid sulfate esters are particularly useful for oral delivery systems. In addition, they may be formulated for topical, intranasal, ophthalmic or parenteral delivery systems.

In another embodiment, the cannabinoid sulfate esters include all possible isomers (stereo or structural) either as individual hemi esters, full esters, salts or mixtures thereof.

In another embodiment, pharmaceutical formulations of cannabinoid sulfate esters, according to the present invention, may include other synergistic ingredients including other cannabinoids, phytochemicals, analgesics and anti-inflammatories.

When compared to other cannabinoids, the present invention discloses cannabinoid compounds with improved PK and PD profiles, including, but not limited to, better stability, solubility and taste, efficient absorption and distribution, and potency, which may provide effective disease control and therapeutic effects.

DESCRIPTION OF THE INVENTION

This disclosure relates to cannabinoid compounds, in particular, cannabinoid sulfate esters that can act as cannabinoid drugs or prodrugs, to methods of producing cannabinoid sulfate esters, to edible, beverage, and pharmaceutical formulations of these compounds, to methods of modulating CB1 and CB2 activity by administering cannabinoid sulfate esters to a patient, and to methods of treating pain, inflammation, neurodegenerative disorders, cancer, renal fibrosis, epilepsy and other motor dysfunction, obesity and other metabolic disorders, addiction, sleep disorders, anxiety, multiple sclerosis, anorexia and other conditions by administering cannabinoid sulfate esters to a patient.

The cannabinoid sulfate esters, according to the present invention, or their active metabolites may act as ligands for either or both CB1 or CB2 or exert their actions through a non-receptor mediated mechanism(s). Due to the unique pharmacokinetics of certain exemplary embodiments of the present invention, some embodiments may be used as biased modulators (agonists, antagonists, partial agonists, inverse agonists, etc.) to selectively bind to a first cannabinoid receptor over a second cannabinoid receptor, such as CB1, CB2, or any other endocannabinoid receptors in a subject. They may also modulate other targets and receptors including, but not limited to, COX enzymes, fatty acid amide hydrolase (FAAH), transient receptor potential cation channel subfamily V (TrpV), peroxisome proliferator-activated receptors, putative abnormal-cannabidiol receptor, ion channels, ligand gated ion channels and other G-protein coupled receptors.

The term "esters" includes all possible hemiesters, full esters, salts and isomers, including, stereoisomers, enantiomers, diastereomers, tautomers, and mixtures, by any ratio(s), thereof. Preferably, the esters are hemiesters or salts. Preferably, they are salts of pure compounds.

The term "cannabinoid" relates to a cannabinoid with at least one hydroxyl group. It includes endogenous, synthetic or natural cannabinoids, including: delta-9-tetrahydrocannabinol (THC), delta-8-tetrahydrocannabinol (THC), cannabidiol (CBD), cannabinodiol (CBND), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), cannabitriol (CBT), and derivatives and analogues of these compounds.

The terms "hydroxyl" group relates to alcoholic or phenolic OH or their isosteres (e.g., SH or $NH_2$).

The term "salts" refers to alkali metal salts, including sodium, potassium, lithium, calcium, or magnesium salts. The term "salts" also refers to salts of organic bases with pKa more than 3, including: cyclic or acyclic amines (e.g. trimethyl amine, erbumine), ethanol amine derivatives (triethanol amine), basic amino acids (e.g. arginine, lysine), amino sugar (e.g. glucosamine), aromatic or aliphatic amines (e.g. aniline, 4-aminopyrimidine) or other cyclic nitrogen compounds (e.g. aziridine, azetidine, diazetidine, imidazoline, pyrazolidine, 3-pyrroline, triazole, imidazole, pyrrolidine, piperidine, pyridine, piperazine, pyridazine, pyrimidine, pyrazine, morpholine, thiomorpholine dioxide, thiazine, pyrrolizidine, azaindole, azaindazole, purine, pyrazolo pyrimidine, quinoline, decahydroquinoline, azocane).

The term "pro-drug" is intended to include esters of the target compounds that may require activation within the human body. The esters may be active (equipotent or more potent) or inactive compounds. Preferably, they are active. Upon administration to human or animal subjects, they undergo enzymatic or chemical activation to release the free drug.

The term "pharmaceutical formulation", as used herein, refers to a mixture of one or more of the compounds described herein, or pharmaceutically acceptable salts thereof, or other synergistic compounds along with other physiologically acceptable carriers and excipients. The purpose of a pharmaceutical formulation (e.g. solid or liquid dosage forms) is to facilitate administration of a compound to a subject animal or human.

The term "subject" in the present disclosure refers to human patients, but is not limited to humans and may include animals.

In a preferred embodiment, the cannabinoid sulfate esters of the present invention are represented by the examples in Formula V. Preferably, the cannabinoid sulfate esters are in the form of potassium or sodium salts. More preferably, in the form of a sodium salt. Alternatively, the cannabinoid sulfate ester is in the form of the salts of morpholine or piperazine or triethanol amine or erbumine, preferably, the salts of piperazine or triethanol amine.

Formula V

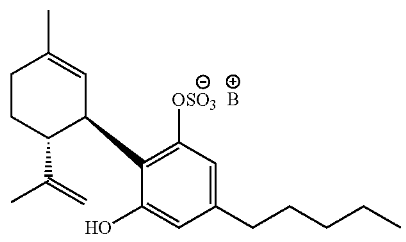

| entry | Base (B) | Description |
|---|---|---|
| 1 | 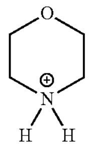 | amorphous white powder |
| 2 | 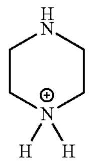 | amorphous white powder |
| 3 | 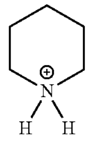 | amorphous yellow powder |
| 4 | 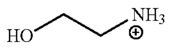 | yellow oil |
| 5 | 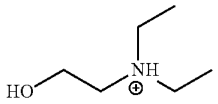 | yellow oil |
| 6 | 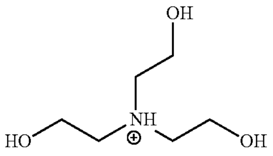 | colorless oil |
| 7 | 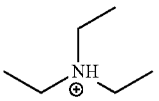 | reddish brown powder |
| 8 | $Na^+$ | brown powder |

The side groups R in formula I to III may be H, another cannabinoid, other active ingredients, or inactive groups. The other cannabinoid is preferably THC or CBD, but may be any other cannabinoid with a hydroxyl, amino, or phenolic functional group. Examples of suitable cannabinoids include, cannabinodiol (CBND), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), and cannabitriol (CBT), or derivatives or analogues of these compounds. The other active ingredient is preferably acetaminophen or ibuprofen, but may include opioids or other medications with at least one hydroxyl, amino, or phenolic functional group. The inactive group is preferably H, but may be methyl, ethyl, or another acyclic saturated hydrocarbon group (i.e. $C_nH_{2n+1}$), aryl or another cyclic saturated hydrocarbon group (i.e. $C_nH_{2n-1}$), or their isosteres and analogues.

The side groups, represented by B in Formulas IV to VI, may be an alkali metal, a cyclic amine, an acyclic amine, an aromatic amine, an aliphatic amine, an amino acid, or an amino sugar. The alkali metal is preferably Na, but may be K, Li, Ca, or Mg. The acyclic amine is preferably triethanol amine, erbumine, arginine, or lysine, but may be, ammonia, triethyl amine, trimethyl amine, tripropyl amine, tributyl amine, and other related amines and derivatives including primary, secondary, and tertiary. The aromatic amine is preferably aniline or 4-aminopyrimidine, but may be naphthylamine, sulfanilic acid, 4-amino benzoic acid, and other related amines, analogues, and derivatives. The side group may also preferably be piperazine or morpholine, but may be aziridine, azetidine, diazetidine, imidazoline, pyrazolidine, 3-pyrroline, triazole, imidazole, pyrrolidine, piperidine, pyridine, pyridazine, pyrimidine, pyrazine, thiomorpholine dioxide, thiazine, pyrrolizidine, azaindole, azaindazole, purine, pyrazolo pyrimidine, quinoline, decahydroquinoline, azocane, or their derivatives, analogues, and isosteres.

The cannabinoid sulfate esters can be prepared by synthetic, semisynthetic, microbial, enzymatic and synthetic biology methods, as well as by genetic manipulation of *Cannabis* sp. Preferably, they can be prepared according to the reaction described in Formulas VII and XI, from any cannabinoid with at least one hydroxyl group. Preferably, the cannabinoid is THC or CBD, and the hydroxyl group is a phenolic OH. Modification of the reaction condition(s) can produce other derivatives and analogues.

Pharmaceutical formulations may be prepared including the cannabinoid sulfate esters or any pharmaceutically acceptable salts thereof, and one or more pharmaceutically acceptable carriers or excipients. Preferably the formulation is a solid or liquid dosage form for oral and oromucosal applications.

The pharmacokinetic profile of certain exemplary embodiments of the cannabinoid sulfate esters is more favourable than the corresponding parent cannabinoids. For example, the $C_{max}$ (maximum plasma concentration) of certain exemplary cannabinoid sulfate salts was 5-fold higher than the parent cannabinoids. As a result, pharmaceutical formulations may contain lower effective doses of these cannabinoid sulfate ester salts, as compared to the parent cannabinoids. In addition, exemplary cannabinoid sulfate ester salts have less variable absorption than the parent cannabinoids. The PK profile of certain exemplary cannabinoid sulfate esters, including the half-life ($T_{1/2}$), maximum plasma concentration ($C_{max}$), and time to reach $C_{max}$ ($T_{max}$), is shown compared to CBD in the table below.

| | CBD | CBD sulfate sodium salt | CBD sulfate piperazinium salt | CBD sulfate morpholinium salt |
|---|---|---|---|---|
| $T_{1/2}$ (h) | 3.9 | 2.9 | 3.0 | 32.7 |
| Cmax (ng/mL) | 4.8 | 12.0 | 19.0 | 10.0 |
| Tmax (h) | 0.5 | 1.0 | 1.0 | 1.0 |

The enzymatic and chemical stability of certain exemplary embodiments of the sulfate ester salts under simulated stomach and intestinal media is more favourable than the corresponding parent cannabinoids. For example, CBD can be released within a short time under simulated stomach and intestinal media (5% to 20% released within 10 to 30 minutes). Exemplary cannabinoid sulfate ester salts also show favourable toxicity profiles compared to the corresponding parent cannabinoids. Further, certain exemplary cannabinoid sulfate ester salts show an aqueous solubility of 5000 to 30000-fold higher than the parent cannabinoids.

The formulation may also contain synergistic ingredients, in addition to active ingredients, which may include: delta-9-tetrahydrocannabinol (THC), delta-8-tetrahydrocannabinol (THC), cannabidiol (CBD), cannabinodiol (CBND, cannabinol (CBN) cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), cannabitriol (CBT), *Boswellia* sp., including *Boswellia carterii* and *Boswellia serrata*, ginger, capsaicin, camphor, polyphenols, including quercetin, ellagic acid, curcumin, and resveratrol, phytosterols, carbohydrates, including mannose-6-phosphate; essential oils, including thymol, and carvacrol, terpenoids, including squalene, lycopene, p-cymene, linalool, and derivatives and analogues thereof, or mixtures or combinations thereof. Preferably, the formulation contains only one medicinal ingredient, being the selected cannabinoid sulfate ester compound(s).

The designed compounds, according to the present invention, can be delivered by oromucosal, nasal, oral, ophthalmic, transdermal and parenteral routes. Preferably, they are delivered by oral routes.

The cannabinoid sulfate esters, according to the present invention, may be used in various applications, including edibles, beverages and medical applications. Preferably, they may be used for the treatment of inflammation and pain, and other related conditions that respond to modulation of cannabinoid receptors. Compared to some other related analogues, preferred embodiments of the salts of these sulfate esters are more stable and water soluble with improved absorption, as well as optimized pharmacokinetic and pharmacodynamic profiles. They may be useful in the treatment of inflammation, pain and related conditions to quickly alleviate the symptoms and provide long-lasting relief to the patient.

EXAMPLES

Example 1: Preparation of Pyridine Salt of CBD Sulfate Ester

A reaction tube with a rubber cap, Teflon septum and stir bar is charged with cannabidiol (CBD) (1.58 g, 5 mmol, 1 equiv), Py·SO3 (97%) (0.96 g, 6 mmol, 1.2 equiv) and 3 mL dry pyridine. The reaction tube is flushed with argon gas and heated at 70° C. for 4 hr, under a pressure of 5-20 barr in a Monowave 50® by Anton Paar. After cooling to room temperature, pyridine is evaporated at reduced pressure (100 mbar) and 50° C. to give the desired product as a viscous oil (2.36 g, quantitative yield). Optionally, the product may be used directly in the method of example 2, below, without purification. When other solvents (such as dichloromethane or tetrahydrofuran), room temperature, or atmospheric pressure were utilized, lower yields were obtained (<50%). When higher temperatures (>100° C.) were used, decompositions were observed.

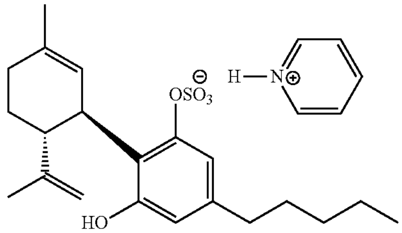

pyridin-1-ium (1'R,2'R)-6-hydroxy-5'-methyl-4-pentyl-2'-(prop-1-en-2-yl)-1',2',3',4'-tetrahydro-[1,1'-biphenyl]-2-yl sulfate: 1H NMR (60 MHz, $CD_3OD$) δ ppm 8.79 (d, J=5.49 Hz, 2H), 8.50 (d, J=7.94 Hz, 1H), 8.01 (t, J=6.56 Hz, 2H), 6.08-7.16 (m, 2H), 5.30 (br. s., 1H), 4.44 (br. s., 2H), 3.75-4.22 (m, 1H), 2.67-3.15 (m, 1H), 1.77-2.57 (m, 6H), 1.64 (s, 6H), 1.34 (br. s., 6H), 0.71-1.01 (m, 3H); $^{13}C$ NMR δ 157.67, 153.34, 150.34, 146.52, 144.41, 142.62, 133.57, 128.31, 127.02, 118.17, 113.92, 111.00, 110.65, 46.42, 38.50, 36.63, 32.77, 32.03, 31.80, 30.82, 23.88, 23.69, 19.55, 14.52; HRMS m/z for $C_{21}H_{29}O_5S^-$, calculated: 393.1741, found: 393.1740.

Example 2: General Procedures for Counter Ion Exchange

Optionally, the pyridine counter ion of the product of the method of example 1, above, may be replaced by other selected bases in quantitative yield (95-99%) and analytical purity (95-98%) as amorphous powder when stirred with 1.2 equiv of the selected base in aqueous solution, according to the following method. The aqueous solution may be 1:1 mixture of ethanol: water, methanol: water, pyridine: water, and/or isopropanol: water. Alternatively, water may be mixed with other organic solvents such as acetone, THF, or chloroform. When the counter ion exchange reactions runs in non aqueous solutions (e.g., absolute ethanol or methanol, or dry pyridine), the target sulfates were obtained in crystalline form. The bases may be selected from NaOH, KOH, LiOH, $Ca(OH)_2$, $Mg(OH)_2$, a cyclic or acyclic amine (e.g. trimethyl amine, erbumine), ethanol amine derivatives (e.g. triethanol amine, diethyl ethanol amine), an aromatic or aliphatic amine (e.g. aniline, 4-aminopyrimidine), an amino acid or amino sugar, or another cyclic nitrogen compound (e.g. aziridine, azetidine, diazetidine, imidazoline, pyrazolidine, 3-pyrroline, triazole, imidazole, pyrrolidine, piperidine, pyridine, piperazine, pyridazine, pyrimidine, pyrazine, morpholine, thiomorpholine dioxide, thiazine, pyrrolizidine, azaindole, azaindazole, purine, pyrazolo pyrimidine, quinoline, decahydroquinoline, azocane). For certain exemplary embodiments, the products produced in crystalline forms are insoluble in water, while the products in amorphous forms are more soluble in water than the parent cannabinoid.

A reaction vial with polyethylene plug and stir bar is charged with pyridinium CBD sulfate, which is preferably produced according to the method of example 1 (0.47 g, 1 mmol, 1 equiv), a selected base (1.2 mmol, 1.2 equiv) and 5 mL of H2O or ethanol or H2O:ethanol solution (1:1). The reaction is stirred at rt for 2-4 hr to produce a milky emulsion which is cooled down to −80° C., and the solvents are freeze-dried, preferably using FreeZone® 2.5 Liter Benchtop Freeze, to give the desired product as amorphous powder in quantitative yields without the need for further purification. The following exemplary CBD sulfate ester salts may be produced according to the method of example 2, by selecting the appropriate base to mix with the pyridinium CBD sulfate in solution.

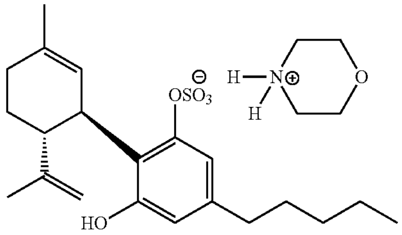

morpholin-4-ium (1'R,2'R)-6-hydroxy-5'-methyl-4-pentyl-2'-(prop-1-en-2-yl)-1',2',3',4'-tetrahydro-[1,1'-biphenyl]-2-yl sulfate: $^1H$ NMR (60 MHz, $CD_3OD$) δ ppm 6.08-7.20 (m, 2H), 5.34 (br. s., 1H), 4.44 (br. s., 2H), 4.10-4.22 (m, 1H), 3.76-3.92 (m, 4H), 3.06-3.22 (m, 4H), 2.80-3.95 (m, 1H), 1.79-2.57 (m, 6H), 1.66 (s, 6H), 1.10-1.40 (m, 6H), 0.81-0.99 (m, 3H); $^{13}C$ NMR δ 157.63, 153.15, 150.30, 142.62, 133.65, 127.06, 118.29, 113.96, 110.96, 108.46, 65.29, 46.38, 45.02, 38.54, 36.71, 32.81, 32.03, 31.76, 30.78, 23.84, 23.69, 19.51, 14.52; HRMS m/z for $C_{21}H_{29}O_5S^-$, calculated: 393.1741, found: 393.1740.

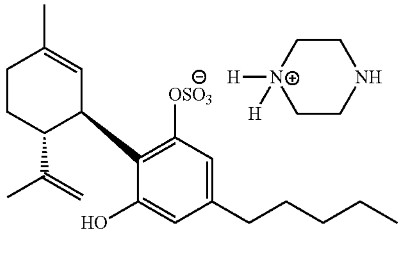

piperazin-1-ium (1'R,2'R)-6-hydroxy-5'-methyl-4-pentyl-2'-(prop-1-en-2-yl)-1',2',3',4'-tetrahydro-[1,1'-biphenyl]-2-yl sulfate: 1H NMR (60 MHz, $CD_3OD$) δ ppm 6.42-7.17 (m, 2H), 5.32 (br. s., 1H), 4.43 (br. s., 2H), 3.95-4.13 (m, 1H), 3.08 (s, 8H), 2.66-2.83 (m, 1H), 1.79-2.56 (m, 6H), 1.65 (s, 6H), 1.10-1.40 (m, 6H), 0.79-0.96 (m, 3H); $^{13}C$ NMR δ 152.95, 150.34, 142.66, 132.99, 127.80, 126.63, 125.89, 118.17, 114.08, 111.04, 46.42, 44.20, 38.70, 36.52, 32.58, 31.80, 30.55, 24.08, 23.53, 19.47, 14.52; HRMS m/z for $C_{21}H_{29}O_5S^-$, calculated: 393.1741, found: 393.1740.

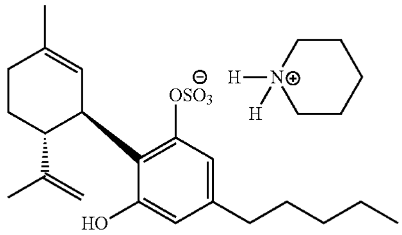

piperidin-1-ium (1'R,2'R)-6-hydroxy-5'-methyl-4-pentyl-2'-(prop-1-en-2-yl)-1',2',3',4'-tetrahydro-[1,1'-biphenyl]-2-yl sulfate: 1H NMR (60 MHz, $CD_3OD$) δ ppm 6.09-7.20 (m, 2H), 5.33 (br. s., 1H), 4.44 (br. s., 2H), 3.95-4.13 (m, 1H), 3.03-3.11 (m, 5H), 2.03-2.49 (m, 6H), 1.67 (s, 12H), 1.10-1.40 (m, 6H), 0.79-0.98 (m, 3H); $^{13}C$ NMR δ 157.67, 153.19, 150.30, 142.58, 133.65, 127.10, 118.13, 113.96, 111.00, 108.46, 46.42, 45.91, 38.54, 36.75, 32.81, 32.07, 31.84, 30.82, 23.88, 23.73, 23.22, 19.55, 14.52.

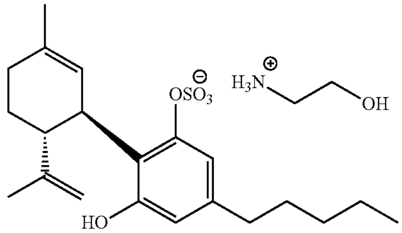

2-hydroxyethan-1-aminium (1'R,2'R)-6-hydroxy-5'-methyl-4-pentyl-2'-(prop-1-en-2-yl)-1',2',3',4'-tetrahydro-[1,1'-biphenyl]-2-yl sulfate: 1H NMR (60 MHz, $CD_3OD$) δ ppm 6.08-7.18 (m, 2H), 5.33 (br. s., 1H), 4.43 (br. s., 2H), 3.95-4.13 (m, 1H), 3.72 (t, J=5.04 Hz, 2H), 2.98 (t, J=5.19 Hz, 3H), 1.08-2.53 (m, 6H), 1.65 (s, 6H), 1.10-1.39 (m, 6H), 0.79-0.98 (m, 3H); $^{13}C$ NMR δ 157.64, 153.23, 150.26, 142.39, 133.69, 127.06, 118.05, 113.92, 110.96, 108.46, 59.25, 46.42, 43.07, 38.50, 36.71, 32.81, 32.03, 31.76, 30.78, 23.88, 23.69, 19.51, 14.52.

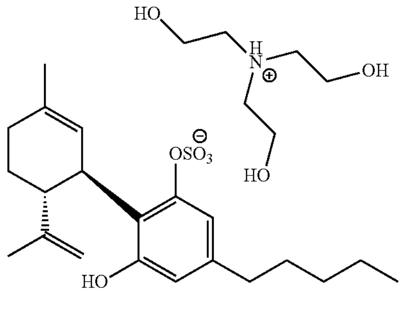

tris(2-hydroxyethyl)ammonium (1'R,2'R)-6-hydroxy-5'-methyl-4 pentyl-2'-(prop-1-en-2-yl)-1',2',3',4'-tetrahydro-[1,1'-biphenyl]-2-yl sulfate: 1H NMR (60 MHz, $CD_3OD$) δ ppm 6.02-7.26 (m, 2H), 5.30 (br. s., 1H), 4.44 (s, 2H), 3.94-4.26 (m, 1H), 3.05-3.94 (m, 15H), 2.86-2.99 (m, 1H), 1.81-2.49 (m, 6H), 1.65 (s, 6H), 1.10-1.44 (m, 6H), 0.75-1.03 (m, 3H); $^{13}C$ NMR δ 157.60, 153.15, 150.46, 142.58, 134.35, 127.45, 117.98, 113.96, 110.65, 108.46, 57.57, 57.30, 46.42, 37.61, 36.71, 32.77, 32.11, 31.80, 30.82, 23.84, 23.69, 19.51, 14.52.

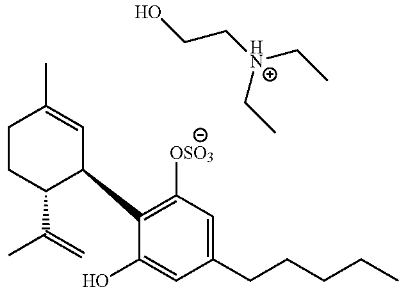

N,N-diethyl-2-hydroxyethan-1-aminium (1'R,2'R)-6-hydroxy-5'-methyl-4 pentyl-2'-(prop-1-en-2-yl)-1',2',3',4'-tetrahydro-[1,1'-biphenyl]-2-yl sulfate: $^1H$ NMR (60 MHz, $CD_3OD$) δ ppm 6.08-7.19 (m, 2H), 5.32 (br. s., 1H), 4.43 (br. s., 2H), 3.95-4.15 (m, 1H), 3.77-3.93 (m, 2H), 3.43-3.72 (m, 1H), 3.08-3.30 (m, 6H), 2.89 (br. s., 1H), 1.80-2.65 (m, 6H), 1.66 (s, 6H), 1.30 (t, J=7.33 Hz, 12H), 0.80-0.97 (m, 3H); $^{13}C$ NMR δ 157.63, 153.27, 150.30, 142.54, 132.44, 127.69, 117.94, 113.92, 111.00, 108.46, 56.91, 54.96, 49.03, 46.42, 38.74, 36.71, 32.81, 32.03, 30.82, 23.88, 23.69, 19.55, 14.52, 9.18.

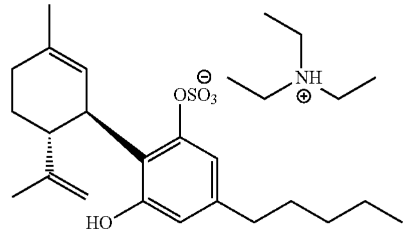

triethylammonium (1'R,2'R)-6-hydroxy-5'-methyl-4 pentyl-2'-(prop-1-en-2-yl)-1',2',3',4'-tetrahydro-[1,1'-biphenyl]-2-yl sulfate: $^1H$ NMR (60 MHz, $CD_3OD$) δ ppm 6.08-7.19 (m, 2H), 5.31 (br. s., 1H), 4.45 (s, 2H), 3.82-4.11 (m, 1H), 3.01-3.35 (m, 6H), 2.88 (br. s., 1H), 1.81-2.45 (m, 6H), 1.65 (s, 6H), 1.17-1.40 (m, 15H), 0.80-0.97 (m, 3H); $^{13}C$ NMR δ 157.64, 153.31, 150.30, 142.54, 134.28, 127.49, 117.94, 113.92, 110.65, 108.46, 48.02, 46.42, 37.61, 36.71, 32.77, 32.07, 31.84, 30.86, 23.88, 23.73, 19.55, 14.52, 9.37.

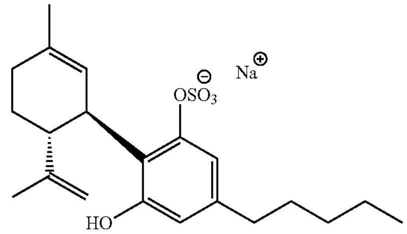

sodium (1'R,2'R)-6-hydroxy-5'-methyl-4 pentyl-2'-(prop-1-en-2-yl)-1',2',3',4'-tetrahydro-[1,1'-biphenyl]-2-yl sulfate: 1H NMR (60 MHz, $CD_3OD$) δ ppm 6.51-7.13 (m, 2H), 5.12-5.36 (m, 1H), 4.42 (br. s., 1H), 3.70-3.77 (m, 2H), 3.30-3.38 (m, 1H), 2.00-2.82 (m, 6H), 1.61 (br. s., 6H), 1.06-1.30 (m, 6H), 0.87-0.072 (m, 3H); $^{13}C$ NMR δ 155.66, 150.87, 150.36, 143.26, 134.37, 126.73, 123.65, 121.15, 117.88, 110.39, 46.13, 37.55, 34.70, 30.60, 30.41, 30.14, 29.94, 23.00, 21.95, 18.36, 13.80; HRMS m/z for $C_{21}H_{29}O_5S^-$, calculated: 393.1741, found: 393.1740.

Example 3: Preparation of Morpholine Salt of THC Sulfate Ester

To a stirred solution of chlorosulfonic acid (582 mg, 5 mmol) and delta-9-THC (314.5 mg, 1 mmol) in 2 mL dry toluene (at rt for 20 min), add 1 mL dry morpholine and heat the mixture 30 to 70° C. and stir until reaction completion (1 hr). Filter off and recrystalize the resulting precipitate from aqueous MeOH (1:1) to yield 300 mg delta-9-THC sulfate morpholine salt.

Example 4: Preparation of Piperazine Salt of THC Sulfate Ester

To a stirred solution of chlorosulfonic acid (582 mg, 5 mmol) and delta-9-THC (314.5 mg, 1 mmol) in 2 mL dry toluene (at rt for 20 min), add 1 mL dry piperazine and heat the mixture to 70° C. and stir until reaction completion (1 hr). Filter off and recrystalize the resulting precipitate from aqueous MeOH (1:1) to yield 300 mg delta-9-THC sulfate piperazine salt.

Example 5: Preparation of THC Hemi Sulfate Ester Under Enzymatic Condition

Dissolve THC (0.027 g, 0.088 mmol) in 600 μL acetone and add 5 mL Tris-glycine (100 mM, pH 9). Add 500 μL of 12 U/ml arylsulfotransferase (AST) to the milky solution. Stir the resulting solution (1 unit/ml, 1.6 μM AST, 15 mM THC) and add N-hydroxysuccinimide sulfate Na salt (0.021 g, 0.1 mmol). Repeat the addition 3 times every hour. After 4 h, add acetic acid to pH 6 and then evaporate the reaction mixture to dryness. Solubilize the residue in 15 mL methanol and add 5 g silica gel. Evaporate again to dryness and pour the silica gel onto a silica column and elute with acetonitrile (0.5% acetic acid/5% to 10% methanol). N-hydroxysuccinimide is eluted first, followed by THC hemi sulfate as a pure salt (0.03 g, 95% isolated yield).

The present invention has been described and illustrated with reference to an exemplary embodiment; however, it will be understood by those skilled in the art that various changes may be made, and equivalents may be substituted for elements thereof without departing from the scope of the invention as set out in the following claims. Therefore, it is intended that the invention is not limited to the embodiments disclosed herein.

What is claimed is:

1. A cannabinoid compound, comprising a sulfate or hemisulfate ester of a cannabinoid having at least one hydroxyl group or pharmaceutically acceptable salts thereof;

wherein when the cannabinoid is delta-9-tetrahydrocannabinol (THC) or delta-8-tetrahydrocannabinol (THC), the salts are not with KOH or pyridinium; and wherein when the cannabinoid is cannabidiol (CBD) and when the salts are with NaOH, the cannabinoid compound is a mono-sulfate or hemisulfate ester.

2. The cannabinoid compound of claim 1, wherein the cannabinoid is selected from the group consisting of: delta-9-tetrahydrocannabinol (THC), delta-8-tetrahydrocannabinol (THC), cannabidiol (CBD), cannabinodiol (CBND), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), and cannabitriol (CBT), and their derivatives, analogues, and related chemical structures.

3. The cannabinoid compound of claim 2, wherein the salts are with at least one inorganic or organic base selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

4. The cannabinoid compound of claim 2, wherein the cannabinoid compound is a sulfate or hemisulfate ester of THC, represented by formula I:

Formula I

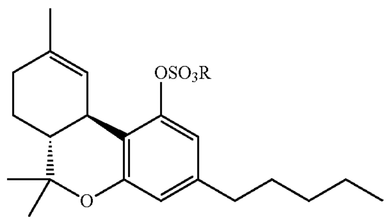

wherein R is selected from the group consisting of: H, a second cannabinoid, a synergistic compound, a non-synergistic active compound, and an inactive side group.

5. The cannabinoid compound of claim 2, wherein the cannabinoid compound is a sulfate or hemisulfate ester of CBD, represented by the formula II:

Formula II

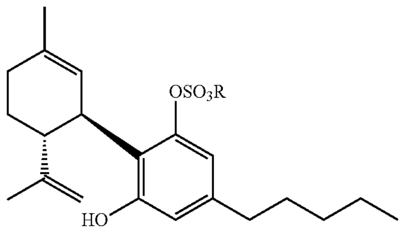

wherein R is selected from the group consisting of: H, a second cannabinoid, a second active compound, and an inactive side group.

6. The cannabinoid compound of claim 2, wherein the cannabinoid compound is a sulfate or hemisulfate ester of CBD, represented by the formula III:

Formula III

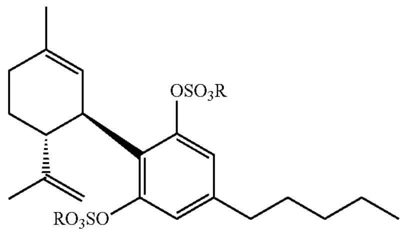

wherein R is selected from the group consisting of: H, a second cannabinoid, a second active compound, and an inactive side group.

7. The cannabinoid compound of claim 3, wherein the cannabinoid compound is a sulfate ester salt of THC, represented by the formula IV:

Formula IV

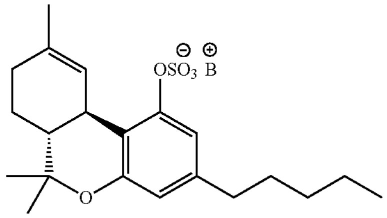

wherein B is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

8. The cannabinoid compound of claim 7, wherein B is selected from the group consisting of: NaOH, KOH, LiOH, triethanol amine, erbumine, arginine, ammonia, triethyl amine, trimethyl amine, tripropyl amine, tributyl amine, aniline, 4-aminopyrimidine, aphthylamine, sulfanilic acid, 4-amino benzoic acid, piperazine, morpholine, aziridine, azetidine, diazetidine, imidazoline, pyrazolidine, 3-pyrroline, triazole, imidazole, pyrrolidine, piperidine, pyridine, pyridazine, pyrimidine, pyrazine, thiomorpholine dioxide, thiazine, pyrrolizidine, azaindole, azaindazole, purine, pyrazolo pyrimidine, quinoline, decahydroquinoline, and azocane.

9. The cannabinoid compound of claim 3, wherein the cannabinoid compound is a sulfate ester salt of CBD, represented by the formula V:

Formula V

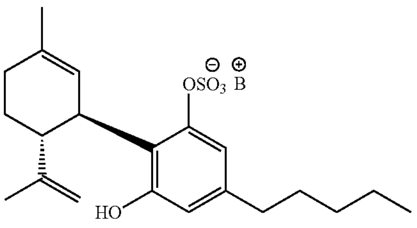

wherein B is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

10. The cannabinoid compound of claim 9, wherein B is selected from the group consisting of: NaOH, KOH, LiOH, triethanol amine, erbumine, arginine, ammonia, triethyl amine, trimethyl amine, tripropyl amine, tributyl amine, aniline, 4-aminopyrimidine, aphthylamine, sulfanilic acid, 4-amino benzoic acid, piperazine, morpholine, aziridine, azetidine, diazetidine, imidazoline, pyrazolidine, 3-pyrroline, triazole, imidazole, pyrrolidine, piperidine, pyridine, pyridazine, pyrimidine, pyrazine, thiomorpholine dioxide, thiazine, pyrrolizidine, azaindole, azaindazole, purine, pyrazolo pyrimidine, quinoline, decahydroquinoline, and azocane.

11. The cannabinoid compound of claim 10, represented by the formula $V_1$.

Formula $V_1$

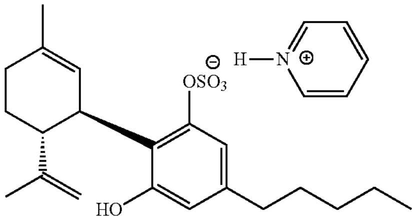

.

12. The cannabinoid compound of claim 10, represented by the formula $V_2$.

Formula $V_2$

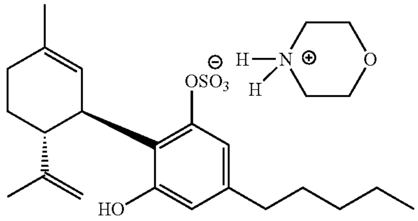

.

13. The cannabinoid compound of claim 10, represented by the formula $V_3$.

Formula $V_3$

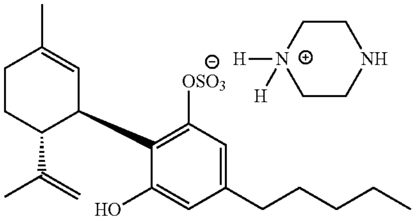

.

14. The cannabinoid compound of claim 10, represented by the formula $V_4$.

Formula $V_4$

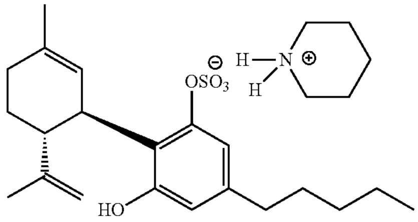

.

15. The cannabinoid compound of claim 10, represented by the formula $V_5$.

Formula $V_5$

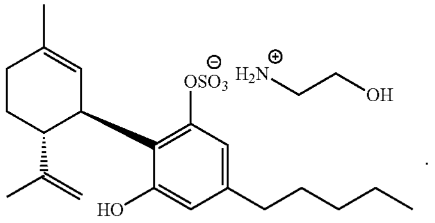

16. The cannabinoid compound of claim 10, represented by the formula $V_6$.

Formula $V_6$

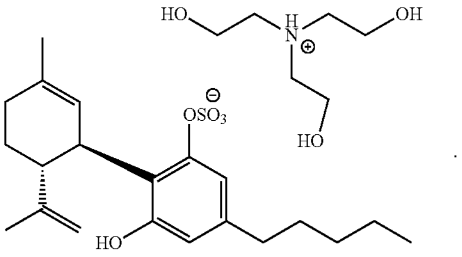

17. The cannabinoid compound of claim 10, represented by the formula $V_7$.

Formula $V_7$

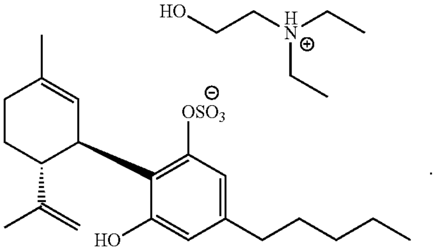

18. The cannabinoid compound of claim 10, represented by the formula $V_8$.

Formula $V_8$

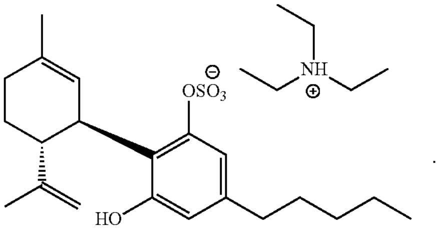

19. The cannabinoid compound of claim 10, represented by the formula $V_9$.

Formula $V_9$

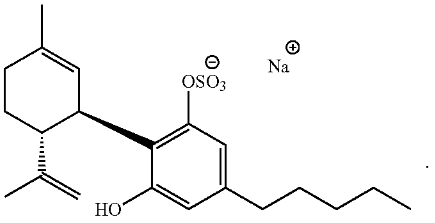

20. The cannabinoid compound of claim 10, represented by the formula $V_{10}$.

Formula $V_{10}$

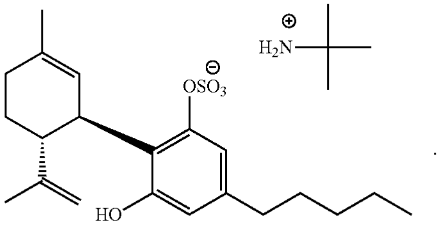

21. The cannabinoid compound of claim 10, represented by the formula $V_{11}$.

Formula $V_{11}$

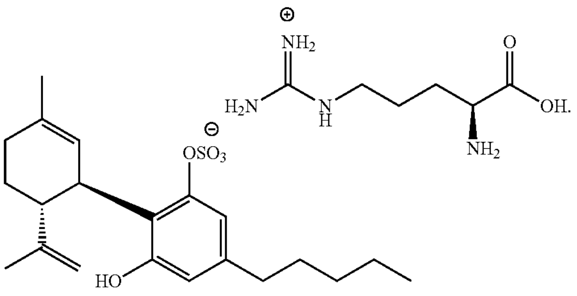

22. The cannabinoid compound of claim 10, represented by the formula $V_{12}$.

Formula $V_{12}$

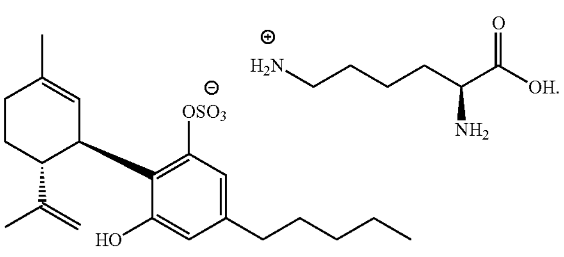

23. The cannabinoid compound of claim 3, wherein the cannabinoid compound is a sulfate ester salt of CBD, represented by the formula VI:

Formula VI

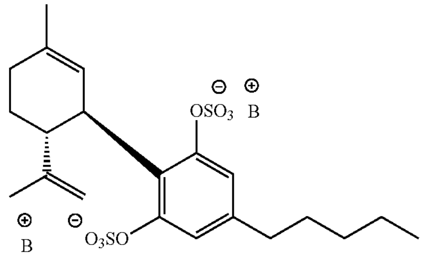

wherein B is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

24. The cannabinoid compound of claim 23, wherein B is selected from the group consisting of: Na, K, Li, triethanol amine, erbumine, arginine, ammonia, triethyl amine, trimethyl amine, tripropyl amine, tributyl amine, aniline, 4-aminopyrimidine, aphthylamine, sulfanilic acid, 4-amino benzoic acid, piperazine, morpholine, aziridine, azetidine, diazetidine, imidazoline, pyrazolidine, 3-pyrroline, triazole, imidazole, pyrrolidine, piperidine, pyridine, pyridazine, pyrimidine, pyrazine, thiomorpholine dioxide, thiazine, pyrrolizidine, azaindole, azaindazole, purine, pyrazolo pyrimidine, quinoline, decahydroquinoline, and azocane.

25. A method of producing a cannabinoid-containing edible or beverage product, comprising introducing a cannabinoid compound of any one of claims 1 to 24 to an edible or beverage product to produce a cannabinoid-containing edible or beverage product.

26. A method of treating a subject in need thereof, comprising administering to the subject a therapeutically effective amount of a cannabinoid compound of any one of claims 1 to 24 as a drug or prodrug in a pharmaceutical formulation.

27. A biased agonist of a first cannabinoid receptor over a second cannabinoid receptor, comprising a cannabinoid compound of any one of claims 1 to 24.

28. A method of producing a cannabinoid compound, comprising the steps of:

a. dissolving a cannabinoid having at least one hydroxyl group in a suitable aprotic organic solvent to produce a cannabinoid solution;
b. reacting the cannabinoid solution with a sulfate transfer reagent in the presence of an alkali or an organic base;
c. heating the reaction under conventional heating, microwave heating, or sonication to produce a product; and
d. purifying the product using flash chromatography, extraction, distillation, sublimation, or crystallization.

29. The method of claim 28, wherein the aprotic organic solvent is selected from the group consisting of pyridine, toluene, tetrahydrofuran, halogenated hydrocarbons, xylenes, and hexanes.

30. The method of claim 29, wherein sulfate transfer reagent is selected from the group consisting of protected and free chlorosulfonic acid, protected and free sulfonic acid, protected and free sulfuric acid, sulfur trioxide, sulfur trioxide complexes, sulfur trioxide pyridine, alkali metal disulfate, sulfonyl imidazolium salts, N-hydroxysuccinimide-sulfate and tributylsulfoammonium betaine.

31. The method of claim 30, wherein the cannabinoid is selected from the group consisting of: delta-9-tetrahydrocannabinol (THC), delta-8-tetrahydrocannabinol (THC), cannabidiol (CBD), cannabinodiol (CBND), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerol monoethyl ether (CBGM), cannabielsoin (CBE), and cannabitriol (CBT), and their derivatives, analogues, and related chemical structures.

32. The method of claim 31, wherein the alkali or organic base is selected from the group consisting of: NaOH, KOH, LiOH, $Ca(OH)_2$, $Mg(OH)_2$, erbumine, a cyclic amine, an acyclic amine, an ethanol amine derivative, an aromatic amine, an aliphatic amine, an amino sugar, and an amino acid.

33. The method of claim 32, wherein the steps (b) and (c) are carried out at a pressure above atmospheric pressure.

34. The method of claim 33, wherein the cannabinoid is CBD, the alkali or organic base is pyridine, and the product is the pyridine salt of CBD sulfate ester, and wherein the reaction is heated to a temperature between 65° C. and 90° C. at a pressure of between 5 and 20 bar, and wherein the reaction time is between 2 and 4 hours.

35. The method of claim 34, further comprising the following steps:

a. dissolving the product in an aqueous solution of water and one or more organic solvents selected from the group consisting of: ethanol, methanol, isopropanol, pyridine, acetone, THF, and chloroform to produce a product solution;
b. reacting the product solution in the presence of a second alkali or organic base to produce a second product; and
c. purifying the second product using flash chromatography, extraction, distillation, sublimation, or crystallization.

36. The method of claim 34, further comprising the following steps:

a. dissolving the product in a non aqueous solution of one or more organic solvents selected from the group consisting of: ethanol, methanol, isopropanol, pyridine, acetone, THF, and chloroform to produce a product solution;
b. reacting the product solution in the presence of a second alkali or organic base to produce a second product; and
c. purifying the second product using flash chromatography, extraction, distillation, sublimation, or crystallization.

37. A method of producing a cannabinoid compound, comprising reacting a cannabinoid having at least one hydroxyl group in the presence of N-hydroxysuccinimide sulfate and arylsulfotransferase at a pH of between 8.5 and 9 for a reaction time of at least 12 hours.

38. The cannabinoid compound of claim 7, wherein B is glucosamine.

39. The cannabinoid compound of claim 9, wherein B is glucosamine.

40. The cannabinoid compound of claim 23, wherein B is glucosamine.

* * * * *